(12) United States Patent
Bottner et al.

(10) Patent No.: US 7,406,856 B2
(45) Date of Patent: Aug. 5, 2008

(54) CHROMIUM/TITANIUM OXIDE SEMICONDUCTOR GAS SENSOR AND METHOD FOR PRODUCTION THEREOF

(75) Inventors: Harald Bottner, Freiburg (DE); Jurgen Wollenstein, Bad Emstal (DE); Gerd Kuhner, Freiburg (DE)

(73) Assignee: Fraunhofer-Gesellschaft zur Forderung der Angewandten Forschung e.V., Munich (DE)

( * ) Notice: Subject to any disclaimer, the term of this patent is extended or adjusted under 35 U.S.C. 154(b) by 960 days.

(21) Appl. No.: 10/489,574

(22) PCT Filed: Sep. 2, 2002

(86) PCT No.: PCT/EP02/09763

§ 371 (c)(1),
(2), (4) Date: Apr. 20, 2004

(87) PCT Pub. No.: WO03/023387

PCT Pub. Date: Mar. 20, 2003

(65) Prior Publication Data

US 2004/0231974 A1    Nov. 25, 2004

(30) Foreign Application Priority Data

Sep. 12, 2001   (DE) ................................ 101 44 900

(51) Int. Cl.
G01N 7/00   (2006.01)
(52) U.S. Cl. ..................................... 73/31.06
(58) Field of Classification Search ............... 73/31.06
See application file for complete search history.

(56) References Cited

U.S. PATENT DOCUMENTS

| 4,967,589 A | * | 11/1990 | Yagawara et al. .......... 73/23.25 |
| 5,003,812 A | * | 4/1991 | Yagawara et al. .......... 73/31.06 |
| 5,918,261 A | | 6/1999 | Williams et al. |

FOREIGN PATENT DOCUMENTS

| DE | 44 24 342 C1 | 11/1995 |
| DE | 197 10 456 C1 | 8/1998 |
| DE | 197 18 584 C1 | 11/1998 |
| DE | 199 44 410 C2 | 4/2001 |
| EP | 1 067 377 A2 | 1/2001 |
| GB | 2 202 948 A | 10/1998 |
| WO | WO 00/24677 | 5/2000 |
| WO | WO 01/38867 A1 | 5/2001 |

OTHER PUBLICATIONS

Baratto, C. et al.; "Front-side Micromachined porous silicon nitrogen dioxide gas sensor"; Thin Solid Films; 391, Elsevier Sequoia, S.A., Jul. 16, 2001, pp. 261-264.

(Continued)

*Primary Examiner*—Hezron Williams
*Assistant Examiner*—Rodney Frank
(74) *Attorney, Agent, or Firm*—Barnes & Thornburg LLP

(57) ABSTRACT

A metal oxide semiconductor gas sensor and a method for production thereof. The sensor comprises a sensor-active metal oxide thin layer applied to a substrate, in contact with at least one electrode. The sensor-active metal oxide thin layer comprises a chromium/titanium oxide (CTO) layer with a thickness of about 10 nm to about 1 µm. The chromium and titanium layers are applied over each other using thin layer technology and are subsequently tempered.

12 Claims, 4 Drawing Sheets

OTHER PUBLICATIONS

Henshaw, G.S. et al.; "Selectivity and Composition Dependence of Response of Gas-sensitive Resistors"; Part 2.-Hydrogen Sulfide Response of $Cr_{2-x}Ti_xO_{3+y}$: J. Mater. Chem., 1995, 5(11), pp. 1791-1800.

Jayaraman, V. et al.; "Preparation and characterisation of $Cr_{2-x}Ti_xO_{3+\delta}$ and its sensor properties"; Sensors and Actuators B 55, Elsevier Sequoia, S.A., May 11, 1999, pp. 175-179.

Li, Yongxiang et al.; "Gas Sensing Properties of P-type Semiconducting Cr-doped $TiO_2$ Thin Films"; Transducers '01. Eurosensors XV. 11TH International Conference on Solid-State Sensors and Actuators. Digest of Technical Papers, Proceedings of 11TH International Conference on Solid State Sensors and Actuators Transducers '01 Eurosensors, XV, Munich, Germany, Jun. 10-14, 2001; pp. 840-843.

Sberveglieri, G.; "Recent developments in semiconducting thin-film gas sensors", Sensors and Acuators B 23, Elsevier Sequoia, S.A., Feb. 1, 1995, pp. 103-109.

Sberveglieri, G. et al.; "$Sn_{1-x}Fe_xO_y$: a new material with high carbon monoxide sensitivity" Sensors and Acuators B Chemical B20, Nos. 2/3; Jun. 1994, pp. 163-167.

Sharma, Rajnish K. et al.; "Mechanism of highly sensitive and fast response Cr doped $TiO_2$ oxygen gas sensor", Sensors and Acuators B Chemical B45, 1997, pp. 209-215.

\* cited by examiner

CHROMIUM/TITANIUM OXIDE SEMICONDUCTOR GAS SENSOR AND METHOD FOR PRODUCTION THEREOF

CROSS-REFERENCE TO RELATED APPLICATIONS

This application is a U.S. national counterpart application of international application serial no. PCT/EP02/09763 filed Sep. 2, 2002, which claims priority to German application serial no. 101 44 900.3 filed Sep. 12, 2001.

BACKGROUND AND SUMMARY OF THE INVENTION

The invention pertains to a metal oxide semiconductor gas sensor, which has a chromium/titanium oxide (CTO) layer as a sensor-active thin metal oxide layer, and a process for its manufacture.

Metal oxide semiconductor gas sensors are known, and are used in many sectors for detecting particles in the air. Semiconductor gas sensors generally comprise a sensor-active metal oxide layer that is arranged on a substrate, whereby the sensor-active layer is connected to at least one electrode. The earlier sensors are preferably constructed in such a way in this regard that contact electrodes are applied directly to an inert support. The sensor-active layer is then deposited onto the contact electrodes. An integrated heating unit is usually provided in order to adjust to the operating temperature, whereby this heating unit can be arranged, for example, on the rear side of the substrate. A thin $SiO_2$ layer, for example, is provided for passivation purposes both for the contact electrodes and for the heating unit, whereby this thin silica layer can be applied directly to the substrate. In this regard, use is also often made, in a controlled manner, of promotors/catalysts for specifically activating a gas reaction at or on the surface. Sensors that have been modified in this way are used for a plurality of gases.

As far as the sensor-active layer is concerned, it is also known that it can be applied by means of thin layer technology. A sensor array with metal oxide semiconductor gas sensors is described in DE 44 24 342 A1, whereby these sensors are operated in the form of resistance elements, and whereby the sensor-active layer is a $SnO_2$ layer that has been applied by means of thin layer technology. Further thin layer gas sensors of this type are also described in DE 197 10 456.8 A1 as well as in DE 197 18 584.3 A1. The following are recommended as metal oxide materials, which are suitable for thin layer technology, in the documents that are described above: $SnO_2$, $TiO$, $ZnO$, $Fe_xO_y$, $ZrO_2$, $Ga_2O_3$, $CuO$, $InO_3$, and $WO_3$.

It is also known from the prior art that use can be made of a layer that comprises a mixed oxide, namely one comprising chromium/titanium oxide (CTO), as a sensor-active layer for gas sensors. However, the manufacture of such sensors, i.e. a gas sensor in which use is made of a mixed oxide of the type described above as a sensor-active layer, has been possible thus far only in the thick layer technology sector.

A disadvantageous feature in this connection is that sensors, which have a CTO layer as a sensor-active layer, do not have any structuring possibilities in the μm region. Thus these gas sensors cannot be introduced, in the form of micro-electronic components, into appropriate circuits.

Starting from here, the problem for the present invention is to propose a metal oxide semiconductor gas sensor that has a mixed oxide as a sensor-active layer, so that it can be introduced, in the form of a micro-electronic component, into appropriate circuits.

A further problem is to indicate a suitable process for the manufacture of such metal oxide semiconductor gas sensors that have a mixed oxide as a sensor-active layer.

The invention therefore pertains to a metal oxide semiconductor gas sensor that has a chromium/titanium oxide layer as a sensor-active thin metal oxide layer. Such a gas sensor, which has a thin CTO layer as a sensor-active layer, has not previously become known from the prior art. Thus now, for the first time, gas sensors with CTO layers can also be incorporated, in the form of microelectronic components, into appropriate circuits. The thin layer sensor with the CTO layer in accordance with the invention has a layer thickness of 10 nm to 1 μm. The layer thickness is preferably selected in such a way that it lies in the range from 100 to 500 nm. Thus the sensor in accordance with the invention involving thin layer technology differs clearly from the previously known sensor of WO 01/38867 A1 that also has a CTO layer as a sensor-active layer because its morphology derives from the sector involving thick layer technology. Thus utilization for microelectronics is not possible.

An essential aspect of the sensor in accordance with the invention is that the mixed oxide is present in the form of a single phase material that has the corundum structure, whereby this phase advantageously corresponds to that of sensors involving thick layer technology. The gas sensor with the thin CTO layer in accordance with the invention can hereby have up to 40 atom-% of titanium in the cation sublattice.

The gas sensors in accordance with the invention with thin CTO layers have specific layer resistances of approximately 10 kΩ to 10 MΩ, and preferably several multiples of 100 kΩ, at operating temperatures of approximately 350° C.

As previously, the CTO layer of the gas sensor in accordance with the invention can of course contain catalysts or promoters that are already known from the prior art.

In the case of the substrates, use can likewise be made of all substrates that were previously known for gas sensors of the prior art. Use is preferably made of silicon as a substrate with $SiO_2$ as an insulator along with $Al_2O_3$ or quartz glass.

The thin layer gas sensor with the CTO layer in accordance with the invention can also have a passivation layer that is arranged between the substrate and the CTO layer. Use is preferably made of $SiO_2$ as a passivation layer for the gas sensor in accordance with the invention. The passivation layer can have a thickness of 100 nm to 1 μm.

The thin layer gas sensor in accordance with the invention is not subject to any restrictions whatsoever in regard to the electrode arrangement. In principle, all structures, which are previously known from the prior art for the production of electrodes, can also be used for the thin layer gas sensor in accordance with the invention. It is preferable in this regard if the sensor is constructed in the form of a contact pad on the substrate. Reference is made to DE 44 24 342 C1 in regard to the design of this contact pad and the corresponding materials. Reference is made exclusively to the disclosed contents of this document [translator: i.e. for the purpose of the present patent document as well].

The invention also comprises the possibility of connecting together several sensors to give a sensor array. In order to do this, reference is also made to the aforementioned DE 44 24 342 C1 and to DE 197 10 4568 A1 and DE 197 18 584.3 [translator: i.e. for the purpose of the present patent document as well]. The possibilities that are pointed out therein for constructing sensor arrays and the structuring thereof also apply to the gas sensor that is described above.

The invention also comprises a process for the manufacture of the metal oxide semiconductor gas sensor that is described above.

An essential aspect in the case of the process in accordance with the invention is that the metal layers are applied one above the other by means of thin layer techniques that are known as such, and that tempering then takes place. It is hereby immaterial which layer is applied first. The chromium layer can be applied to the titanium layer or the titanium layer can be applied to the chromium layer. Surprisingly, the inventors have been able to show that inter-diffusion, reaction, and crystal growth take place simultaneously when the metal layers are applied one above the other as in the above process. It is to be emphasized in this regard that the process in accordance with the invention leads to a single phase material having the corundum structure.

Thin layer processes such as thermal evaporation or sputtering can be used for assembling the layers. Basically, processes such as MOCVD and MBE-derived methods are also extremely suitable.

In this connection, it is immaterial for the thermal processes whether the metals are transformed into the vapor form from suitable evaporator sources by means of resistance heating, or whether the metals are transformed into the vapor phase via the use of electron beam evaporators. For sputtering processes, use can be made of processes with individual metal targets as well as those with suitable mixed targets. Simple and variable process implementation is preferably achievable via individual targets.

The selection of the individual layer thicknesses relative to one another is hereby essential both for pre-adjusting the chromium to titanium ratio and for the formation, in accordance with the invention, of the homogeneous mixed oxide. The layer thicknesses of the individual metal layers preferably lie in the range from 2 to 200 nm, and preferably in the range from 5 to 75 nm.

Appropriate layer thickness ratios for sensitive layers can hereby be derived directly from the molecular data and the density of the metals. Thus it is possible to cover the concentration range up to 40 atom-% of titanium in the cation sublattice, whereby this concentration range is important for sensitive layers.

The layer thickness ratios are limited by the necessity, by means of a subsequent tempering process, of ensuing homogeneous intermixing of the metals via inter-diffusion, and of ensuring complete oxidation to give CTO via oxidative implementation of the tempering process. The coating process itself has to be carried out in such a way that the coating adheres to substrates that are suitable for sensor applications. The coating rates are hereby in the 10-20 nm/minute range. The overall layer thicknesses are governed by the overall resistances in the 10 to 100 $\Omega$ range that are to be achieved at the usual temperature of these layers when used as gas sensors. These are temperatures of up to 500° C.

A further special aspect of the process in accordance with the invention is the tempering process, whereby this is a low temperature process in comparison to the temperatures of up to 1300° C. that are necessary for the formation of homogeneous mixed crystals. This low temperature process, which is suitable for temperatures below and up to 850° C., is possible because—in comparison to the prior art, and as a result of the above designated deposition process—significantly closer molecular contact is present between the participating partners than in the case of a conventional solid state reaction between the prescribed and also nano-scale proportions of the separate oxides $Cr_2O_3$ and $TiO_2$. The essential difference relative to the prior art in regard to the formation of the CTO resides in the aspect that inter-diffusion, reaction, and crystal growth take place simultaneously here. The tempering times are approximately 12 hours. The layer thickness increases during tempering. Tempering can take place both under controlled atmospheres in a conventional diffusion oven and also via rapid thermal annealing equipment.

The process is successfully demonstrated, on the one hand, by means of adhesion studies via temperature shock treatment in liquid nitrogen (detachment of layers that are not in accordance with the invention) and, on the other hand, by means of electron microscopy, preferably by means of scanning electron microscopy (SEM) combined with energy dispersive x-ray analysis (EDX), whereby the latter method is for determining the elemental composition. The crystal structure is successfully demonstrated by means of conventional $\Theta/2\Theta$ x-ray studies. Within the limits of detection, these show none of the metals and exclusively single phase material having the crystal structure that is expected: i.e. the corundum structure.

An essential aspect of all the forms of embodiments with the above designated methods is that, following the tempering process, the CTO has the same advantageous properties as the CTO of the prior art in terms of structure, electrical properties, and sensitive properties.

In forms of embodiment that are typical, the tempered layers, when in a suitable sensor layout (e.g. DE 44 22342 C1, DE 197 10456 C1, DE 197 18584 C1, DE 199 44 410 A1), have specific layer resistances of approximately 10 $\Omega$ to several M$\Omega$, and preferably several multiples of 100 k$\Omega$ at operating temperatures of approximately 350° C.

The invention will be described in more detail below by means of FIGS. 1 through 4.

Figure 4:
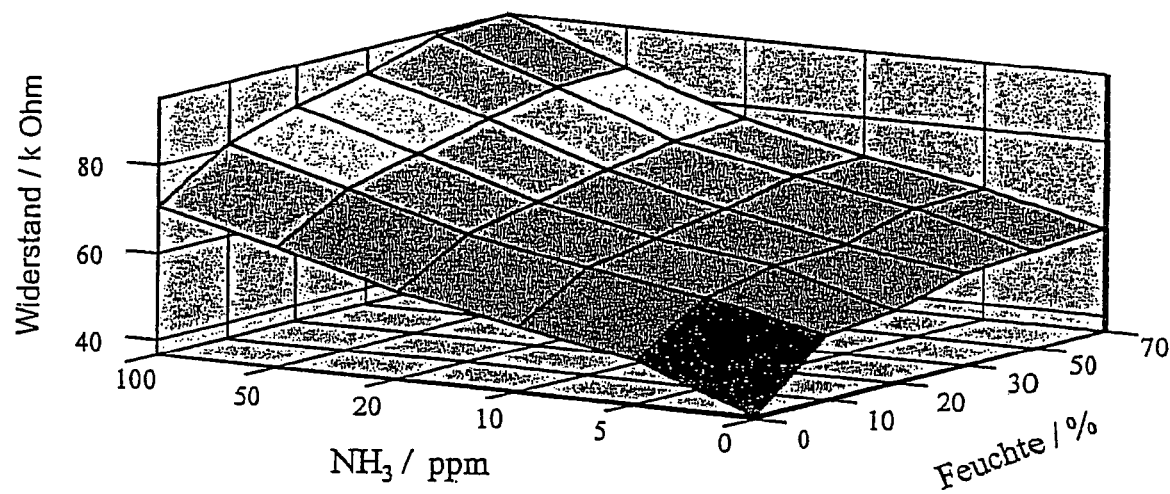

FIG. 4 indicates the dependence of the resistance of a CTO sensor, in accordance with the invention, on the relative atmospheric humidity and on the ammonia concentration.

Figure 1:
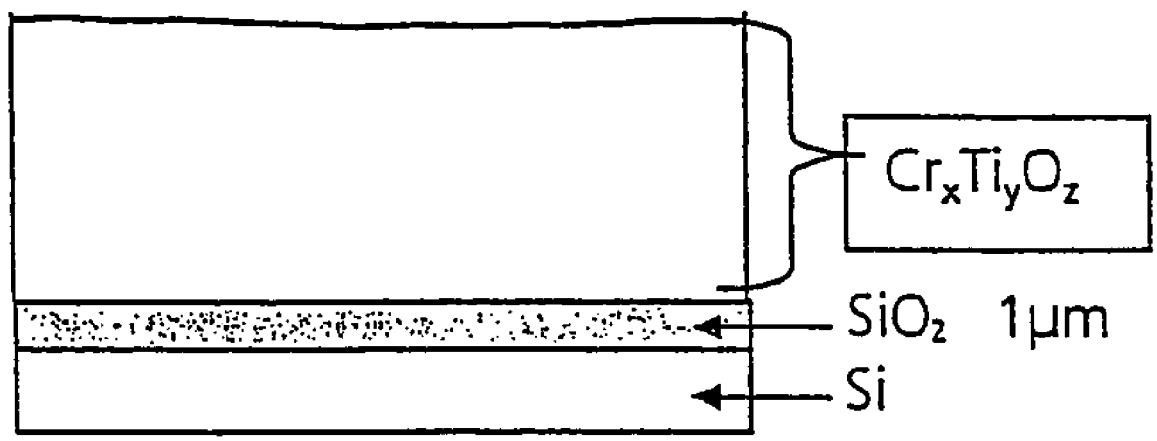
FIG. 1 shows the schematic structure of a thin layer gas sensor in accordance with the invention.

FIG. 1 shows the basic structure, in schematic form, of a sensor in accordance with the invention. FIG. 1 does not hereby contain the necessary electrodes for operating the sensor.

The sensor in accordance with FIG. 1 comprises a silicon substrate onto which a 1 µm thick $SiO_2$ layer has been deposited. The CTO layer has a thickness of several multiples of 100 nm, and was deposited via the process in accordance with the invention as explained above in the specification. In this case, FIG. 1 merely shows a possible form of embodiment by way of example. In exactly the same way, it is also possible to build up the layer structure on other substrates, such as $Al_2O_3$ in its usual morphological forms including sapphire, that are suitable for the particular use in question of the gas sensor.

FIG. 1 hereby shows the layer structure in the form of an individual sensor. As already stated above in the specification, the invention also naturally comprises all other forms of embodiment in which the individual sensor is serially connected in the form of an array. In this regard, reference is explicitly made [for the purpose of the present patent document as well] to the disclosed contents of DE 44 22 342, DE 197 10456 A1, DE 197 18 584 A1, and DE 199 44 410 A. The forms of embodiment that are described therein in the form of an array are also possible with the sensor in accordance with the invention. A preferred form of embodiment comprises an array with SnO$_2$ with and without catalyst[s], with WO$_3$ with and without catalysts, and also with V$_2$O$_5$ with and without catalysts primarily formed for oxide layers using thin layer technology. In exactly the same way, combinations are also possible in the form of an array on a chip with sensitive layers that have been applied using conventional thick layer techniques.

Figure 2:
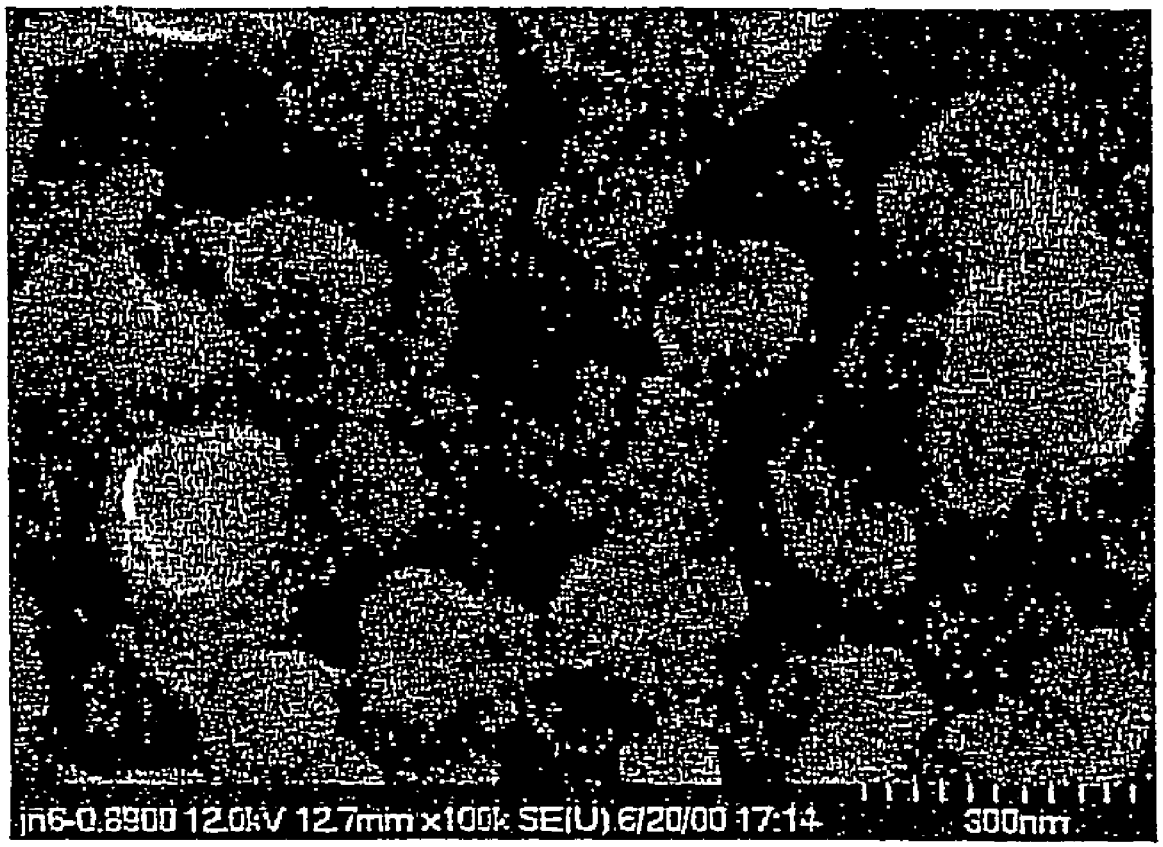
FIG. 2 is a scanning electron microscope photograph of the thin CTO layer in accordance with the invention.

Next, FIG. 2 shows a SEM photograph of a thin layer CTO surface in accordance with the invention. The surface in accordance with FIG. 2 was tempered in synthetic air at 900° C. Crystals of the size order of 50 nm to 200 nm can be seen that are connected to the various faces. As can be seen from FIG. 2, the CTO surface has a uniform structure both in a transverse fracture and in the grains and in the distribution of grain sizes on the surface. The patent applicant has been able to show via experiments that such layers withstand the adhesion test (LN$_2$ shock test).

Figure 3:
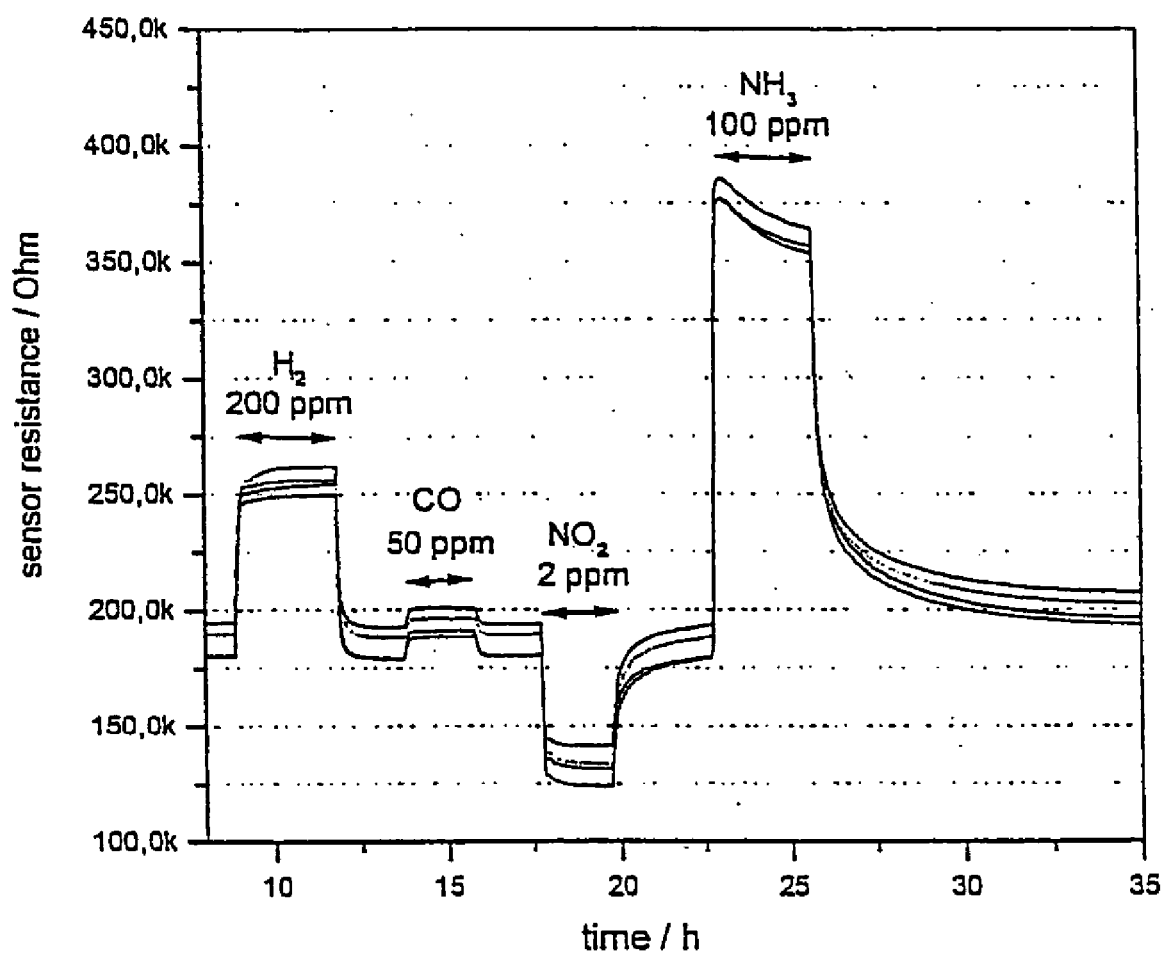
FIG. 3 shows the change in resistance of a CTO sensor element, in accordance with the invention, as a function of time.

Next, FIG. 3 shows an example of characteristics that are typical of a layer in accordance with the invention.

FIG. 3 hereby shows the change in resistance as a function of time in combination with a sensor layout in accordance with DE 197 18 584 when being impacted with various target gases in synthetic air (50% relative humidity) at an operating temperature of 420° C.

The high sensor sensitivity in the case of being impacted with ammonia is to be emphasized in this connection. The slow adjustment to the basic resistance following impacting with ammonia is not engendered by the sensor in this case. Hence only the desorption properties are shown of the measurement equipment that was used here.

In addition to these typical characteristics, the layers in accordance with the invention are also characterized by a typical low sensitivity to humidity at various ammonia concentrations.

FIG. 4 shows the influence of the relative atmospheric humidity at various ammonia concentrations on the resistance of a CTO sensor at an operating temperature of 380° C. In this typical example, the ammonia concentration is 0-100 ppm, and the relative atmospheric humidity has been varied from 0-70%.

The typical properties with respect to conventional target gases, such as methane, CO, NO, H$_2$, and ammonia, combined with the low sensitivity to moisture permits additional forms of embodiment together with a moisture sensor in an array. Such a combination results in the possibility of quantitatively determining the target concentration via the combined sensor reaction comprising sensitivity to the corresponding targets together with low moisture sensitivity by means of subsequent evaluation using a second exclusive[ly] moisture sensitive sensor.

The invention claim is:

1. A metal oxide semiconductor gas sensor comprising a sensor-active thin metal oxide layer that is applied to a substrate, and that is in contact with at least one electrode wherein the sensor-active thin metal oxide layer is a chromium/titanium oxide (CTO) layer with a layer thickness of 100 nm to 500 nm, whereby the mixed oxide is present in the form of a single phase material having a corundum structure.

2. The metal oxide semiconductor gas sensor in accordance with claim 1 wherein the CTO layer has up to 40 atom-% of titanium in the cation sub-lattice.

3. The metal oxide semiconductor gas sensor in accordance with claim 1 wherein the CTO layer has an overall resistance of 5 kΩ to 10 MΩ at about 350° C.

4. The metal oxide semiconductor gas sensor in accordance with claim 3 wherein the overall resistance is in the 10-500 kΩ range.

5. The metal oxide semiconductor gas sensor in accordance with claim 1 wherein at least in part, the CTO layer contains at least one of a catalyst and a promoter.

6. The metal oxide semiconductor gas sensor in accordance with claim 1 wherein the substrate comprises at least one of silicon, Al2O3, sapphire and quartz glass.

7. The metal oxide semiconductor gas sensor in accordance with claim 1 further comprising a passivation layer between the substrate and the CTO layer.

8. The metal oxide semiconductor gas sensor in accordance with claim 7 wherein the passivation layer comprises at least one of SiO2, Si3N4, Al2O3.

9. The metal oxide semiconductor gas sensor in accordance with claim 8 wherein the passivation layer has a layer thickness of from about 100 nm to about 1 μm.

10. The metal oxide semiconductor gas sensor in accordance with claim 1 wherein the sensor is constructed in the form of a contact pad that is applied to the substrate.

11. A sensor array comprising a plurality of metal oxide semiconductor gas sensors constructed according to claim 1 coupled together to form the sensor array.

12. A sensor array according to claim 11 comprising at least two rows arranged in parallel containing a combined total of 3-10,000 metal oxide semiconductor gas sensors.

* * * * *